United States Patent [19]

Harandi et al.

[11] Patent Number: 5,144,085
[45] Date of Patent: Sep. 1, 1992

[54] FEEDSTOCK DEWATERING AND ETHERIFICATION OF CRUDE ETHANOL

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 500,356

[22] Filed: Mar. 28, 1990

[51] Int. Cl.$^5$ ............................................. C07C 41/06
[52] U.S. Cl. ..................................................... 568/697
[58] Field of Search ......................................... 568/697

[56] References Cited

U.S. PATENT DOCUMENTS 4,334,890 6/1982 Kochar et al. .
4,409,406 10/1983 Feldman .
4,665,237 5/1987 Arakawa et al. .
4,814,519 3/1989 Harandi et al. .
4,827,045 5/1989 Harandi et al. .
4,831,195 5/1989 Harandi et al. .

FOREIGN PATENT DOCUMENTS 289232 11/1988 European Pat. Off. ............ 568/697

Primary Examiner—Howard T. Mars
Attorney, Agent, or Firm—Alexander McKillop; Charles J. Speciale

[57] ABSTRACT

Improved process techniques and equipment for reacting crude aqueous ethanol feedstock with iso-olefinic hydrocarbons to produce $C_6^+$ ethyl t-alkyl ethers, which comprises: distilling the aqueous ethanol feedstock; contacting ethanol rich distillate overhead containing a minor amount of water with a liquid hydrocarbon extractant rich in $C_4^+$ isoalkene under liquid extraction conditions; recovering an aqueous phase containing water introduced from the overhead; recovering an organic extract phase comprising the hydrocarbon extractant and a major amount of ethanol introduced in the feedstock; and reacting the extracted ethanol and $C_4^+$ isoalkene in contact with an acid etherification catalyst under catalytic reaction conditions to produce ether product.

10 Claims, 1 Drawing Sheet

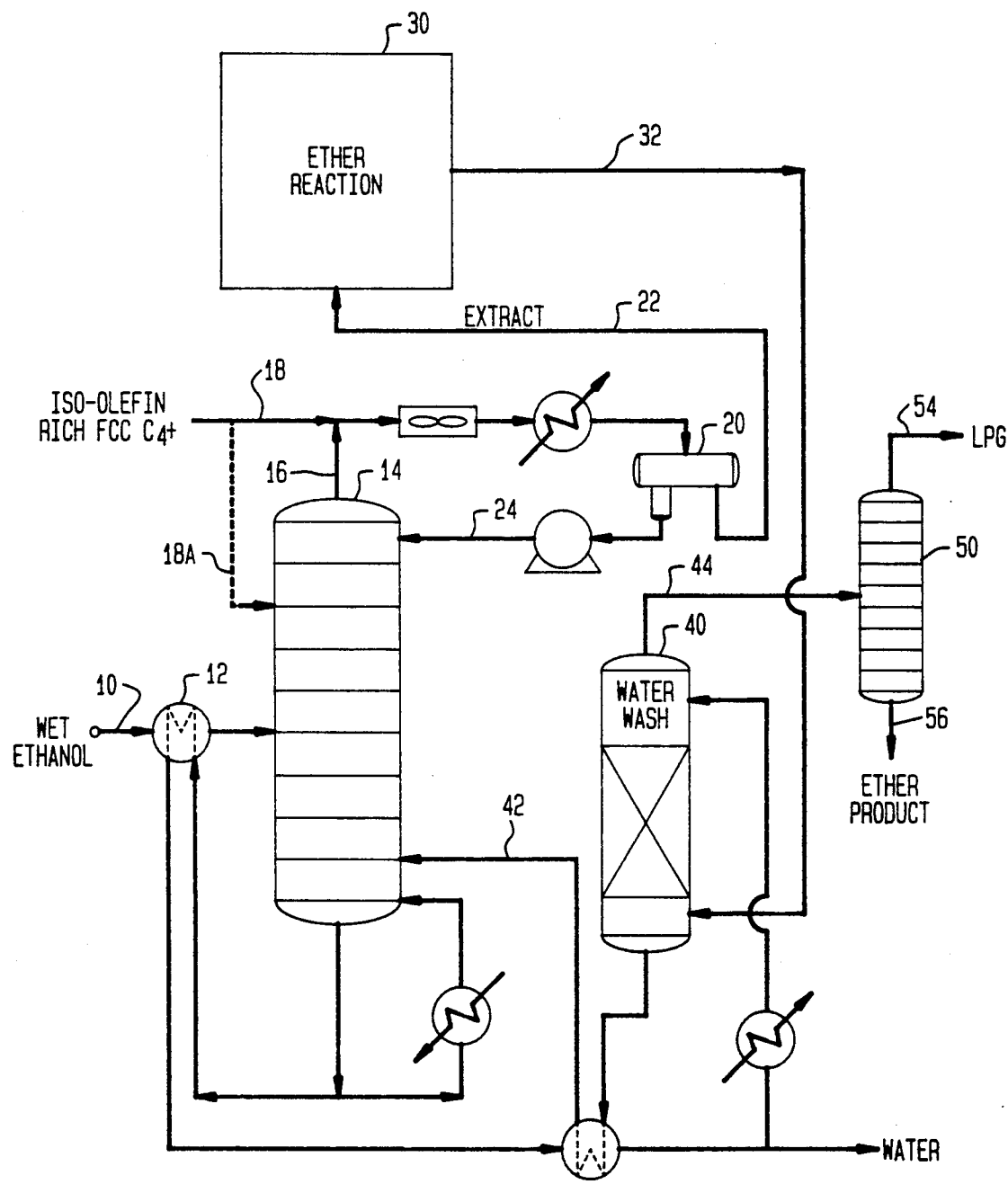

FEEDSTOCK DEWATERING AND ETHERIFICATION OF CRUDE ETHANOL

BACKGROUND OF THE INVENTION

This invention relates to techniques for converting crude ethanol or the like to lower ethyl isoalkyl ethers. In particular, this invention relates to an integrated system for converting crude ethanol to valuable products by etherifying lower branched olefins, such as $C_4$-$C_5$ isoolefins. It is known that isobutylene may be reacted with ethanol over an acidic catalyst to provide ethyl tertiary butyl ether (ETBE) and isoamylenes may be reacted with methanol over an acidic catalyst to produce tertiary-amyl ethyl ether (ETAE). Those ethers having the formula $C_2H_5$—O—R, where R is an isoalkyl radical, are particularly useful as octane improvers for liquid fuels, especially gasoline.

Increasing demand for high octane gasolines blended with lower aliphatic alkyl ethers as octane boosters and supplementary fuels has created a significant demand for tertiary alkylethers, including the $C_6$ and $C_7$ ethyl alkyl ethers, such as ethyl tertiary-butyl ether (ETBE) or ethyl t-amyl ether (ETAE). ETBE and ETAE are known to be high octane ethers. An article by H. E. Buc et al., *S. A. E. Journal* (Transactions), Vol. 39, No. 3, p. 333, discusses the advantages one can achieve by using such material to enhance gasoline octane.

Ethanol may be readily obtained from biomass by fermentation in a known manner. Crude ethanol from such processes usually contains a significant, typically from minor amount of water, amounts up to 90 wt %. Large amounts of water are not generally desirable in etherification due mainly to hydration of olefins.

It is main object of the present invention to provide a novel and economic technique for removing excess water from crude ethanol feedstocks, including novel operating methods and equipment for treating the oxygenate feedstocks prior to etherification.

SUMMARY OF THE INVENTION

A process has been found for reacting crude aqueous ethanol feedstock with iso-olefinic hydrocarbons to produce $C_6+$ ethyl t-alkyl ethers. The improvement herein comprises the steps of:

enriching ethanol from the aqueous feedstock by distillation to provide an ethanol distillate overhead stream containing a major amount of ethanol and a minor amount of water; contacting the aqueous ethanol overhead with a liquid hydrocarbon extractant rich in $C_4+$ isoalkene under liquid extraction conditions;

recovering an aqueous phase containing a minor amount of ethanol and a major amount of water; recovering an organic extract phase comprising the hydrocarbon extractant and a major amount of ethanol introduced in the feedstock; and reacting extracted and distilled ethanol and $C_4+$ isoalkene in contact with an acid etherification catalyst under catalytic reaction conditions to produce ethyl tertiary-alkyl ether product. Advantageously, the prefractionation step is operatively connected with the extraction step to provide means for recycling the extraction raffinate stream as reflux to the prefractionator distillation tower. This technique is particularly useful in obtaining ethanol for etherification containing less than 1.5 wt % water, which cannot be achieved by conventional distillation due to the formation of an azeotrope. The present invention is useful for removing water present in small or large amounts in the feedstock.

These and other objects and features of the invention will be understood from the following description and in the drawing.

DRAWING

The drawing is a schematic etherification process flowsheet depicting the present invention.

DETAILED DESCRIPTION

Typical feedstock materials for etherification reactions include olefinic streams, such as FCC light naphtha and butenes rich in isoolefins. These aliphatic streams are produced in petroleum refineries by catalytic cracking of gas oil or the like. The crude ethanol commercially available from fermentation processes may contain, for instance 50 to 90 wt % water, which must be removed, preferably to a ethanol purity of about 98.5 to 99.5 wt %. It has been found that essentially the entire crude feedstock ethanol content can be recovered by liquid extraction with light olefinic liquid extractant, such as butenes and $C_5+$ light olefinic naphtha. The typical feed ratio range is about 9 to 20 parts hydrocarbon extractant per part by volume of ethanol.

Referring to the drawing, a continuous stream of crude wet ethanol (EtOH) feedstock containing 80 wt % water is introduced via conduit 10 and heat exchanger 12 to a prefractionation distillation column 14 for enriching the ethanol. The overhead vapor stream 16 from tower 14, which can be recovered as an azeotropic mixture of alcohol with at least 5 wt % water, is combined with a liquid hydrocarbon stream 18 rich in isobutylene and/or isoamylene and other $C_4+$ aliphatic components, preferably comprising olefinic crackate light naphtha from a fluidized catalytic cracker.

The combined stream is cooled and passed to extraction unit 20 under extraction conditions, where the liquid phases are separated into an ethanol-rich organic liquid extract stream 22 and aqueous raffinate stream 24 containing a major amount of the water present in the crude feedstream.

The aqueous raffinate stream 24 consists essentially of water, partitioned ethanol and a trace of hydrocarbon. The raffinate provides a reflux for tower 14 where it is introduces in an upper stage. The lighter organic extract phase containing hydrocarbon extraction solvent and the major amount of feedstock ethanol can be recovered from extraction unit 20, preferably with not more than 1.5 wt % water, and introduced under temperature and process conditions suitable for anhydrous conversion of ethanol in contact with etherification catalyst in reactor system 30. From the reactor system 30, the effluent product stream passed to product recovery via line 32. The etherification effluent comprises $C_6+$ ether, unreacted $C_4+$ hydrocarbons and ethanol which are passed via line 32 to a washing tower 40 for contact with water derived from prefractionation tower 14 or from fresh makeup. The washwater aqueous phase bottom stream contains residual amounts of ethanol which can be recycled via line 42, preferably to a lower stage of distillation tower 14. The washed organic liquid phase is passed via line 44 to debutanizer distillation tower 50 where ether product is removed from the system via line 56, along with any unreacted $C_5+$ hydrocarbon in feedstream 18.

Alternatively, it may be desirable to place the debutanizer unit 50 upstream of washing unit 40 in order to reduce the amount of hydrocarbon from the wash tower.

Unreacted C$_4$ hydrocarbons, such as butanes, butenes, etc. are recovered via line 54 substantially free of ethanol.

EXTRACTION UNIT OPERATION

The typical preferred ethanol feedstream material is an azeotropic mixture containing about 5 to 55 volume percent water. The extraction contact unit may be a stirred multi-stage vertical extraction column adapted for continuous operation at elevated pressure. Any suitable extraction equipment may be employed, including cocurrent, cross-current or single contactors, wherein the ethanol feedstream is intimately contacted with a substantially immiscible liquid hydrocarbon solvent, which may be a mixture of C$_4$+ aliphatic components including lower alkanes, n-alkenes or relatively pure isoalkenes, such as isobutylene, etc. This unit operation is described in *Kirk-Othmer Encyclopedia of Chemical Technology* (Third Ed.), 1980, pp. 672–721. Other equipment for extraction is disclosed in U.S. Pat. Nos. 4,827,046 (Harandi and Owen) and 4,334,890 (Kochar et al). The ethanol extraction step can be performed advantageously in a countercurrent multistage design, such as a simple packed column, rotating disk column, agitated column with baffles or mesh, or a series of single stage mixers and settlers.

As an example of typical ethanol extraction with FCC light naphtha in a liquid-liquid contact and separation unit for extracting crude ethanol containing 10 wt % water at about 38° C. (100° F.). The extractor unit and water wash unit are operated at about 35°–80° C. (95°–175° F.) and 100–1000 kPa. The ethanol distillation tower operates at about 100–500 kPa with overhead at about 38°–58° C. and bottoms at about 90°–150° C.

Etherification Operation

The reaction of ethanol with isobutylene and isoamylenes at moderate conditions with an acid catalyst is known technology. The etherification catalyst employed is preferably an ion exchange resin in the hydrogen form or acid zeolite. Numerous acidic catalysts may be employed with varying degrees of success. Typical acidic solid catalysts include sulfonic resins, phosphoric acid modified kieselguhr, silica alumina and medium pore acid zeolites. Typical acid catalysts include Amberlyst 15 sulfonic acid resin and various acid zeolites, such as Zeolite Beta. Processes for producing and recovering ETBE and other lower alkyl t-alkyl ethers from C$_4$-C$_7$ iso-olefins are known to those skilled in the art, such as disclosed in U.S. Pat. Nos. 4,542,250 (Gregory et al), 4,605,787 (Chu et al) and 4,814,519 (Harandi and Owen).

A typical etherification reaction employing the extract phase from the extraction operation described above is provided by reacting the organic stream containing isobutene and ethanol at about 75% conversion in contact with polymeric sulfonic acid resid catalyst (e.g., Amkerlyst 15) at about 65° C. and 1100 kPa.

The present invention is particularly advantageous in the economic dewatering of crude ethanol, thus avoiding expensive and energy-intensive treatment of azeotropic mixtures produced by distillation. By extracting ethanol from the aqueous distillate with hydrocarbon reactant and recycling the raffinate, an effective technique for enriching ethanol azeotrope is achieved. Various modifications can be made to the system, especially in the choice of equipment and non-critical processing steps. While the invention has been described by specific examples, there is no intent to limit the inventive concept as set forth in the following claims.

We claim:

1. In the process for reacting crude aqueous ethanol feedstock with iso-olefinic hydrocarbons to produce C$_6$+ ethyl tertiary alkyl ethers, the improvement which comprises:
   enriching ethanol from the aqueous feedstock in a distillation column to provide an ethanol distillate overhead stream containing a major amount of ethanol and a minor amount of water;
   contacting the aqueous ethanol overhead with a liquid hydrocarbon extractant rich in C$_4$+ isoalkene under liquid extraction conditions;
   recovering an aqueous phase containing a minor amount of ethanol and a major amount of water;
   recovering a substantially water-free organic extract phase comprising the hydrocarbon extractant and a major amount of ethanol introduced in the feedstock;
   reacting ethanol and C$_4$+ isoalkene from the extract phase in contact with an acid etherification catalyst under substantially anhydrous catalytic reaction conditions to produce ethyl tertiary-alkyl ether product; and recycling the aqueous phase as reflux to the distillation column.

2. The improved process according to claim 1 wherein said ethanol distillate overhead stream contains at least 5 wt % water, and wherein the organic extract phase contains not more than about 1.5 wt % water, based on ethanol.

3. The process of claim 1 including the further steps of distilling etherification effluent to recover ethyl t-alkyl ether in a liquid product stream and unreacted C$_4$ light hydrocarbon and ethanol in an overhead stream;
   contacting etherification effluent overhead stream in an effluent washer with at least a portion of liquid water bottoms from feedstock distillation to wash ethanol from the light hydrocarbon effluent; and
   passing ethanol-rich wash water from the effluent washer for codistillation with crude ethanol feedstock.

4. In the process for reacting crude aqueous ethanol feedstock with iso-olefinic hydrocarbons according to claim 1, the further steps of;
   contacting at least a portion of etherification effluent overhead in an effluent washer with at least a portion of liquid water bottoms recovered from feedstock distillation to wash ethanol from the hydrocarbon effluent phase containing ether; and
   passing ethanol-rich wash water from the effluent washer for codistillation with crude ethanol feedstock.

5. In the process for reacting crude aqueous ethanol feedstock with iso-olefinic hydrocarbons according to claim 4 including the step of distilling the hydrocarbon effluent phase to recover ethyl t-alkyl ether and C$_5$+ hydrocarbon in a liquid product stream and unreacted C$_4$ light hydrocarbon in an overhead stream.

6. The process of claim 1 wherein the acid catalyst comprises ion exchange resin.

7. The process of claim 1 wherein the wash water is cofractionated with feedstock to recycle ethanol.

8. The process of claim 1 wherein the feedstock consists essentially of aqueous ethanol containing up to about 90 wt % water, and wherein the extraction liquid comprises a major amount of $C_4$-$C_5$ isoalkenes.

9. The process of claim 1 wherein $C_4+$ hydrocarbons employed in the extraction step comprise olefinic crackate light naphtha from a fluidized catalytic cracker.

10. In the process for reacting crude aqueous ethanol feedstock with iso-olefinic hydrocarbons in $C_4+$ isoalkene to produce $C_6+$ ethyl t-alkyl, an improved feedstock enrichment technique which comprises:

distilling the aqueous ethanol feedstock;

contacting ethanol rich distillate overhead containing a minor amount of water with a liquid olefinic hydrocarbon extractant rich in $C_4+$ isoalkene under liquid extraction conditions;

recovering an aqueous raffinate phase containing water from the distillate overhead; recycling the aqueous raffinate as distillation reflux;

recovering an organic extract phase comprising the hydrocarbon extractant and a major amount of ethanol introduced in the feedstock and containing less than 1.5 wt % water;

reacting the extracted ethanol and $C_4+$ isoalkene in contact with an acid etherification catalyst under catalytic etherification reaction conditions to produce ether product;

distilling etherification effluent to recover ethyl t-alkyl ether in a liquid product stream and unreacted $C_4$ light hydrocarbon and ethanol in an overhead stream;

contacting etherification effluent overhead stream in an effluent washer with at least a portion of liquid water bottoms from feedstock distillation to wash ethanol from the light hydrocarbon effluent; and passing ethanol-rich wash water from the effluent washer for codistillation with crude ethanol feedstock.

* * * * *